United States Patent [19]
Kageyama et al.

[11] Patent Number: 5,160,419
[45] Date of Patent: Nov. 3, 1992

[54] ELECTRODE FOR A COULOMETRIC TYPE OF ELECTROCHEMICAL DETECTOR

[75] Inventors: Yoshiteru Kageyama; Yoshiaki Sawada; Akira Yoshida, all of Yokkaichi, Japan

[73] Assignee: Mitsubishi Petrochemical Company Limited, Tokyo, Japan

[21] Appl. No.: 737,064

[22] Filed: Jul. 29, 1991

[30] Foreign Application Priority Data

Aug. 1, 1990 [JP] Japan ................... 2-204757

[51] Int. Cl.$^5$ ........................................... G01N 27/26
[52] U.S. Cl. ..................................... 204/294; 204/418
[58] Field of Search ....................... 204/400, 294, 418; 502/101, 180

[56] References Cited

U.S. PATENT DOCUMENTS

| | | | |
|---|---|---|---|
| 4,704,193 | 11/1987 | Bowers et al. ................. | 204/418 |
| 4,832,881 | 5/1989 | Arnold, Jr. et al. ............ | 502/180 |
| 5,096,560 | 3/1992 | Takai et al. .................... | 204/294 |

FOREIGN PATENT DOCUMENTS 3610388 10/1987 Fed. Rep. of Germany.
3809624 10/1988 Fed. Rep. of Germany.
1483100 6/1967 France.

OTHER PUBLICATIONS

D. J. Curran et al., "Electrochemical Detector Based on a Reticulated Vitreous Carbon Working Electrode for Liquid Chromatography . . . ", Analytical Chemistry, vol. 56, Apr. 1984, pp. 672-678.

Primary Examiner—John Niebling
Assistant Examiner—Bruce F. Bell
Attorney, Agent, or Firm—Wegner, Cantor, Mueller & Player

[57] ABSTRACT

An electrode for a coulometric type of electrochemical detector, comprising a porous carbon product having the following physical properties (1) to (3):

(1) an average pore size in the range of 5 to 70 μm,
(2) a specific surface area in the range of 0.1 to 3 m$^2$/g, as determined by the BET method, and
(3) a stack thickness of crystallite (Lc(002)) of 40 Å or less, as determined by X-ray diffractometry.

10 Claims, 6 Drawing Sheets

ELECTRODE FOR A COULOMETRIC TYPE OF ELECTROCHEMICAL DETECTOR

BACKGROUND OF THE INVENTION

1. Field of the Invention

This invention relates to an electrode for a coulometric type of electrochemical detector capable of providing a highly sensitive detection of trace amounts of electrically active substances, a process for producing it and an analytical apparatus in which it is built.

2. Background Art

When used in combination with liquid chromatography, electrochemical detectors can detect, with very high sensitivity, trace amounts of electrochemically active substances contained in biopsy such as catecholamines and their metabolites. Thus, analytical apparatuses in which electrochemical detectors are combined with liquid chromatography have been used for the detection and quantitative determination of such electrically active substances.

An amperometric type of electrodes have so far been used as electrodes for electrochemical detectors, but they cannot be applied to more precise analysis because their efficiency of electrolysis is limited. Known as an electrode capable of carrying out detection with the highest sensitivity is one used for a coulometric type of electrochemical detector.

Essentially required for such an electrode for the coulometric type of electrochemical detector is that:

1) it be formed of a porous, electrically conductive material which has higher surface area than a working electrode for an amperometric type of electrolytic cell and which is of an open-pore structure, because it is required that the substances to be detected pass through an electrode cell while they are all electrochemically converted with good efficiency;

2) its surface possess a low polarity and be chemically stable since it is required to show durability during long-term use; and 3) the porous material be required to have a sufficiently large mean pore diameter and a constant pore size distribution so as to reduce as much as possible a pressure difference occurring in the electrode cell, because considerable limitation is imposed on analysis conditions when that pressure difference is in excess during solution passage.

Use of porous carbon materials having a high surface area has been studied as an electrically conductive material expected to meet these condition 1) to 3). For instance, a proposal has been made of an electrode for a coulometric type of electrochemical detector which is formed of a high-surface area, porous graphite, as set forth in U.S. Pat. No. 4,804,455.

However, a graphitic material has a defect of being so poor in chemical stability that it degrades by contact with organic solvents over an extended period. What is generally said of a porous material is that its surface area is in inversely proportional relation to its mean pore diameter or, in other words, the higher its surface area the smaller its mean pore diameter. Thus, in general, even when a graphitic material meets the above condition 1), it will fail to satisfy the condition 3), giving rise to an excessive pressure difference between electrodes and so making it unfit for practical analysis.

In the case of such a graphitic material having a high surface area, the pressure difference occurring during solution passage may be suppressed to some degree by increasing its surface area by forming a number of fine pores of the order of 1 $\mu$m or less on the surface of each of particles constituting the material, while making the distance between particles larger, say 5 $\mu$m or more. With this material, however, it has been found that residual currents are produced owing to penetration of a solution into the fine pores, making the S/N ratio worse. This defect is attributable to the fact that the graphitic material is not glassy or, in better words, the fact that the stack thickness of crystallite, Lc(002), as determined by X-ray diffractometry, is too large, say 80 Å or more. Thus, it has turned out that it is also necessary for the surfaces of porous material forming particles to have a dense structure containing very few fine pores of 1 $\mu$m or less and to be less impregnated with a solution.

Other graphitic materials have been proposed in French Patent No. 1,483,100 and U.S. Pat. No. 4,294,893. However, these materials have been found to have similar defects as referred to in connection with the above-mentioned U.S. Pat. No. 4,804,455.

As proposed in U.S. Pat. Nos. 4,506,028 and 4,814,307, there has also been available a material produced by calcining carbon fibers of 5 to 30 $\mu$m in diameter. This material, which is neither graphitic nor glassy carbon, also has too large an Lc(002), i.e. 80 Å or more, as determined by X-ray diffractometry, again making the S/N ratio worse. In addition, it cannot be used as an electrode over an extended period due to its poor chemical stability.

Moreover, Japanese Patent Laid-open Publication No. 54-41296 discloses a material obtained by calcining carbon black. This material is not a glassy carbon and also not suited for a long-term use as an electrode.

An object of this invention is to provide an electrode for a coulometric type of electrochemical detector designed to produce a pressure difference during solution passage therethrough, which, if any, is too small to place any limitation on the analysis conditions for liquid chromatography and keep the occurrence of residual currents low, thus enabling a highly sensitive detection with a high S/N ratio and exhibiting its improved electrochemical conversion characteristics over an extended period.

Another object of this invention is to provide an analytical apparatus including a column for liquid chromatography and the above-mentioned electrode for a coulometric type of electrochemical detector.

SUMMARY OF THE INVENTION

As a result of intensive studies made to eliminate the above-mentioned defects of the prior art, the present inventors have now found that a porous, carbonaceous material having a specific crystal structure and specific ranges of surface area and average pore diameter can be used to make a working electrode of a coulometric type of detector which meets the above-mentioned conditions, and have thus accomplished this invention.

Thus, the electrode for a coulometric type of detector according to the present invention comprises a porous carbon product having the following physical properties:

(1) an average pore size in the range of 5 to 70 $\mu$m, (2) a specific surface area in the range of 0.1 to 3 $m^2/g$, as determined by the BET method, and (3) a stack thickness of crystallite (Lc(002)) of 40 Å or less, as determined by X-ray diffractometry.

The present inventors have also found that when used in a multi-stage detector system for liquid chromatography, such an electrode enables more sensitive detection than achieved by conventional electrodes.

Thus, the present invention further provides an analytical apparatus comprising a column for liquid chromatography and at least one coulometric type of electrochemical detector, said detector having an electrode comprising a porous carbon product having the following physical properties (1) to (3):

(1) an average pore size in the range of 5 to 70 μm,
(2) a specific surface area in the range of 0.1 to 3 m²/g, as determined by the BET method, and
(3) a stack thickness of crystallite (Lc(002)) of 40 Å or less, as determined by X-ray diffractometry.

DETAILED DESCRIPTION OF THE INVENTION

Figure 1:
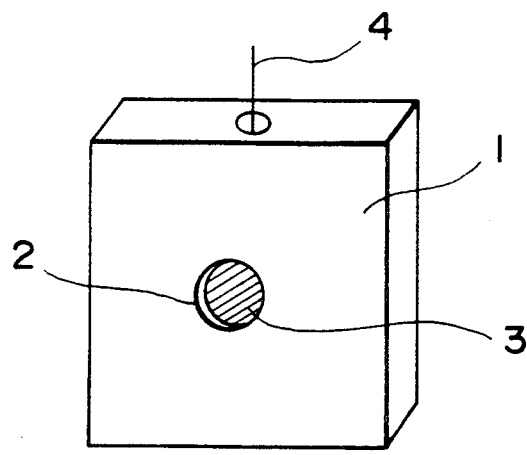
FIG. 1 is a perspective sketch illustrating a working electrode attached in place.

I. Physical Properties of Porous Carbon Product

The porous carbon product used for the electrode for a coulometric type of electrochemical detector according to the present invention comprises the so-called "glassy carbon" in which the stack thickness of crystallite, Lc(002), is 40 Å or less, preferably 20 Å or less, as determined by X-ray diffractometry. When Lc(002) exceeds this range, the glassy carbon degrades in its surface chemical stability so that it cannot maintain its excellent electrochemical conversion properties over an extended period. It is here to be understood that since electrochemical reactions are surface reactions, the above-mentioned requirement for the structure determined by X-ray diffractometry may only be satisfied at least for the surface layer, and may not be satisfied for the internal structure.

It is generally preferred that the specific surface area and the average pore diameter are both relatively large. However, they cannot be excessively large at the same time because, as already mentioned, there is an inversely proportional relation between them, and further the glassy carbon should preferably have a dense surface structure substantially free from any fine pores of 1 μm or below.

In the present disclosure, the "substantially free from any fine pores" is understood to mean that, as will be described later, there is no deterioration of S/N ratios due to the occurrence of residual currents.

The present inventors have found that the abovementioned conditions can satisfactorily be met by a carbon product belonging to a class of glassy carbon having the above-mentioned physical properties and having an average pore diameter in the range of 5 to 70 μm and a specific surface area in the range of 0.1 to 3 m²/g. Thus, the porous carbon product used for the electrode for a coulometric type of electrochemical detector according to the present invention has an average pore size in the range of 5 to 70 μm, preferably 10 to 50 μm and a specific surface area in the range of 0.1 to 3 m²/g, preferably 0.2 to 1 m²/g. Assuming now that the glassy carbon product has a dense surface structure substantially free from any fine pores of 1 μm or below, as determined with a mercury forcing type of porosimeter, with the above-mentioned average pore diameter of 5 to 70 μm, then the specific surface area will fall within the range of 0.1 to 1 m²/g. It is required that relative to this specific surface area, the specific surface area provided by pores of 1 μm or less be at most 3 times, preferably at most 1 time. At higher than 3 times, residual currents come to have a considerable influence upon a drop of S/N ratio, thus making high-sensitivity detection impossible.

It is noted that with an average pore diameter of less than 5 μm, it may be possible to obtain a specific surface area exceeding 3 m²/g. However, there will occur an excessive pressure difference during solution passage with such a small pore size. It is also noted that in the case of a specific surface area less than 0.1 m²/g, the average pore size may be designed to be in excess of 70 μm. However, such a reduced surface area makes the efficiency of electrolysis insufficient.

The specific surface area may be determined by the BET method, and the average pore diameter and the ratio of fine pores may be determined by a mercury forcing type of porosimeter or by microphotography.

The porous carbon product may be obtained, for example, by impregnating a porous material containing pores of an average pore diameter of 10 to 100 μm with a thermosetting resin, and setting said resin, and then calcining and carbonizing the material at a temperature of 1000° C. or higher, preferably 1300° to 2500° C. in a nonoxidizing atmosphere. As the porous material containing pores of an average pore diameter of 10 to 100 μm, use may be made of an aggregate of fibers selected from the group consisting of artificial fibers such as polyamide and phenolic resin fibers and natural fibers such as cotton, paper and pulp. Among others, preference is given to degreased cotton and paper. The thermosetting resin to be used may include furfuryl alcohol resin, phenol formaldehyde resin, acetone/furfural resin and furfuryl alcohol/phenol co-condensation resin.

II. Formation of Electrode

The electrode for a coulometric type of electrochemical detector according to the present invention may be prepared by forming the porous glassy carbon product having the above-mentioned physical properties into a desired shape as by cutting.

Although not critical, the electrode may generally be formed into a columnar shape, which may usually have a diameter of about 2 to 5 mm and a thickness of about 1 to 8 mm, if it is used for liquid chromatography at a flow rate lying in the range of 0.2 to 2 cc/min.

III. Use of the Electrode as Working Electrode

The thus obtained electrode may be used as a working electrode of a coulometric type of detector.

Figure 8:
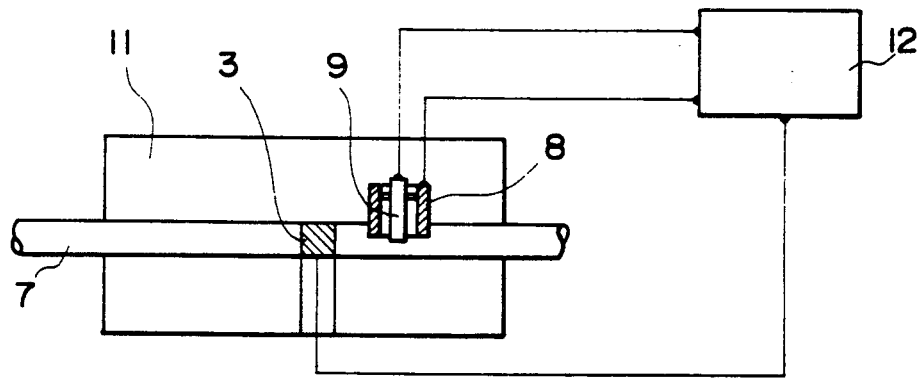
FIG. 8 is a schematic sketch illustrating a coulometric type of electrochemical detector according to this invention.

As illustrated in FIG. 8 by way of example alone, the above-mentioned electrode may be used as a working electrode 3 located in a sample flow path 7.

As shown in FIG. 1 by way of example alone, this electrode may be used as a working electrode 3 fitted into a through-hole 2 formed through a central region of a sheet 1 made of a corrosion-resistant material such as a fluorine-based resin, said through-hole 2 corresponding in shape to the electrode.

A lead wire 4 extending from the working electrode 3 may be formed of any known materials such as platinum. However, particular preference is given to a carbon rod.

The carbon rod may be prepared by cutting a carbonaceous material, e.g. a graphitic or glassy carbon in the form of a rod. As the carbon rod, use may also be made of the lead of a pencil.

Preferably, the carbon rod is 0.5 to 3 mm in diameter and 2 to 30 mm in length.

Connection of the lead 4 to the working electrode 3 is preferably achieved, for example, by forming a hole in the side of the working electrode 3, said hole having an internal diameter slightly smaller than the diameter of the lead 4 used, and screwing the lead 4 into said hole. In this case, the difference between the hole's internal diameter and the diameter of the lead 4 is preferably 0.01 to 0.1 mm.

An electrolytic cell using a carbon rod as the lead 4 of the working electrode 3 can work stably over an extended period without causing electrical contact failure. This is because when the lead is connected to a potentiometer, it is unlikely that the lead may scrape off a portion of the working electrode, at which the lead is held, by a load applied on the lead, thus producing a gap in the junction.

In order to prevent the lead 4 of the working electrode 3 from being damaged by mechanical impact, a portion of the lead 4 extending out of the electrolytic cell may be coated on its surface with an electrically conductive protective material.

The apparatus shown in FIG. 8 includes, in addition to the working electrode 3, a reference electrode 9 and a counter electrode 8, an electrolytic cell 11 housing these electrodes, and a coulometer 12 with a built-in potentiostat for impressing a constant potential between the working and counter electrodes on the basis of the reference electrode.

Figure 2:
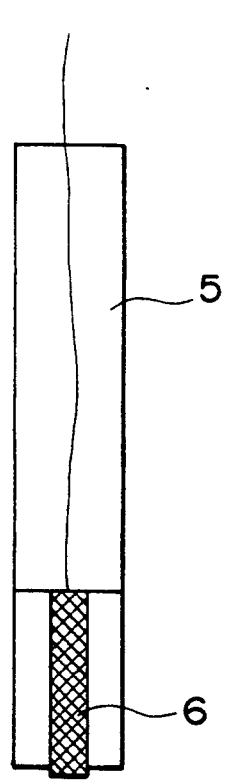
FIG. 2 is a diagrammatic sketch illustrating a reference electrode.

As the reference electrode, use may be made of an ordinary electrode, but preference is given to a silver/silver chloride electrode or an iron ferricyanide/iron ferrocyanide electrode. As illustrated in FIG. 2, the reference electrode, for instance, may be prepared by providing a liquid junction 6 on the tip of a glass tube 5 defining a reference electrode chamber. When using for this liquid junction porous ceramics in place of conventionally known porous glass, the liquid junction is unlikely to clog even after a long-term use and is chemically stable as well. Thus, the porous ceramic liquid junction is greatly advantageous in that it can maintain its excellent electrochemical conversion properties over an extended period either when it is used in contact with an aqueous type of solvent or with an organic type of solvent and it is possible to avoid such close attention as required to handle a porous glass which is poor in mechanical strength.

The porous ceramics, which may be used for the liquid junction, should be those having a pore diameter which is sufficient to enable the liquid in the electrode to penetrate therethrough, such as a sintered compact of alumina, titania, zirconia or their mixtures.

As the counter electrode, use may also be made of an ordinary electrode. For instance, electrodes formed of such corrosion-resistant materials as platinum, gold and stainless steel may preferably be used.

Figure 3:
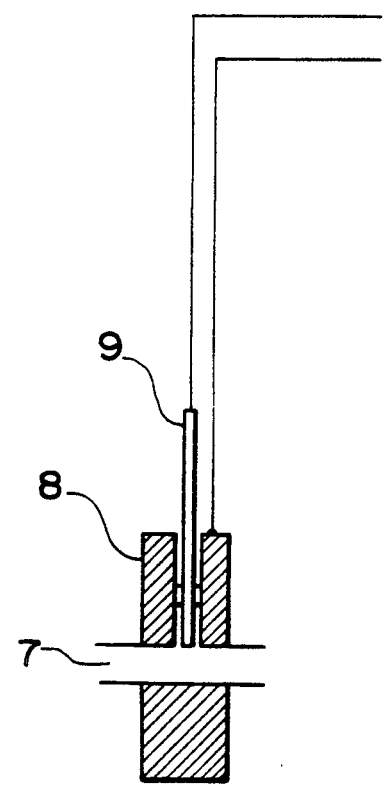
FIG. 3 is a diagrammatic sketch illustrating a composite electrode.
Figure 4:
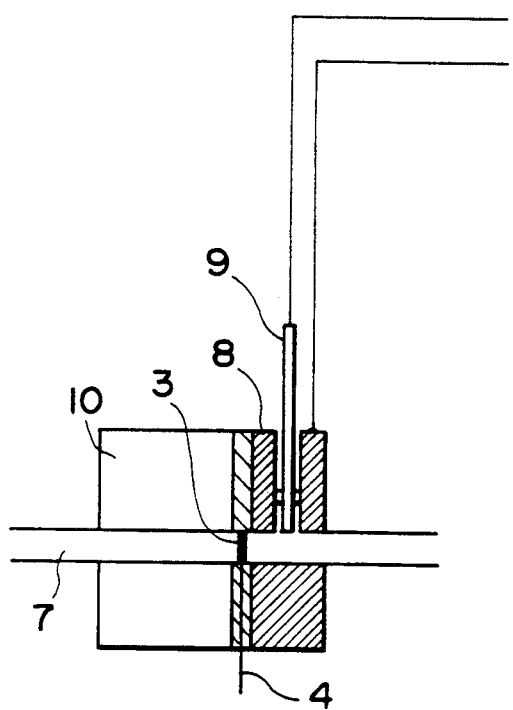
FIGS. 4, 5, 6 and 7 are each a diagrammatic sketch showing a coulometric type of electrolytic cell.
Figure 5:
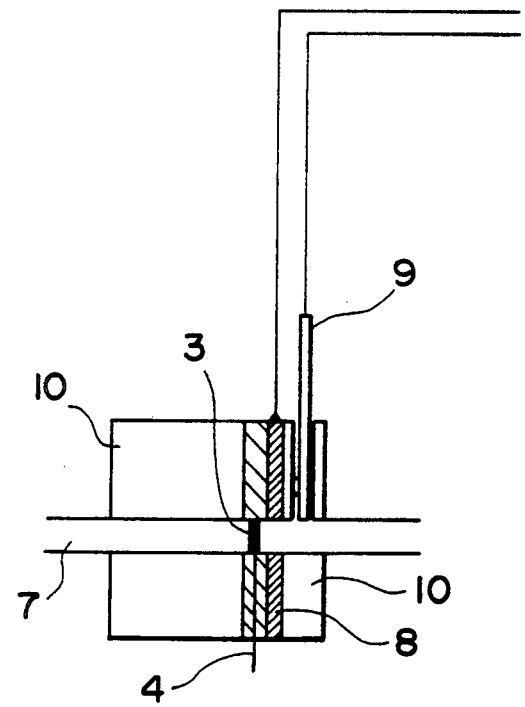
Figure 6:
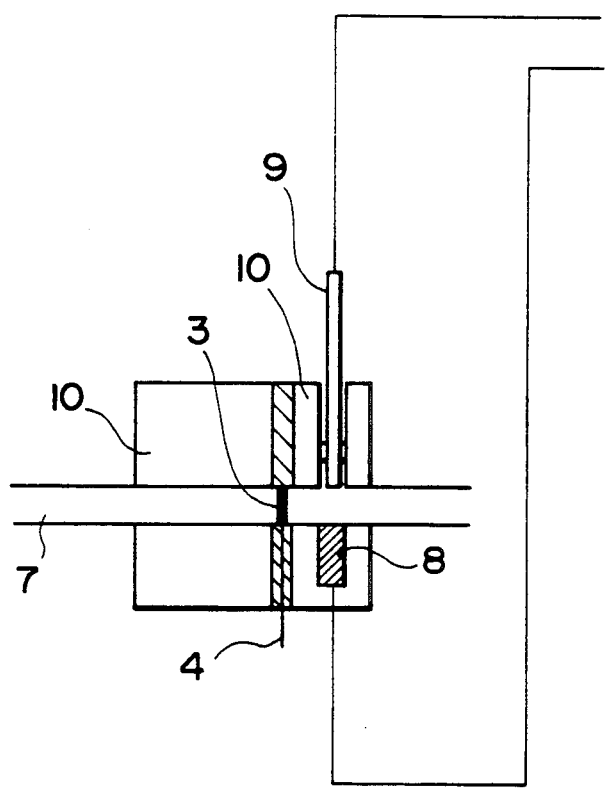
Figure 7:
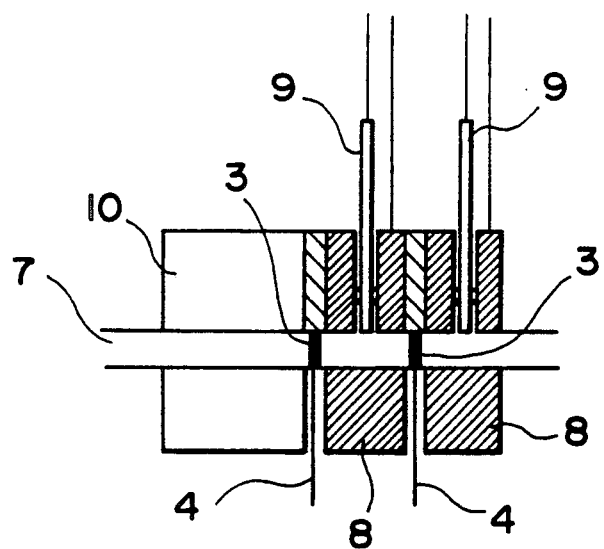

The counter and reference electrodes are preferably used in the form of a composite electrode wherein, as illustrated in FIG. 3 by way of example, a sample flow path 7 is provided transversely through a central region of a stainless steel block, a hole intersecting the sample flow path 7 is provided longitudinally through said block to form a counter electrode 8, and a reference electrode 9 is inserted into this through-hole.

A coulometric type of electrolytic cell including such a composite electrode is smaller in the intracell dead volume than that in which a series arrangement of reference and counter electrodes is disposed along the sample flow path 7, so that when used as a liquid chromatograph detector, it can make the divergence of a peak narrow.

As illustrated in FIGS. 4, 5, 6 and 7 by way of example alone, such an electrolytic cell is constructed of a plastic block 10, a glass sample flow path 7 which is housed in the block 10 together with the counter and reference electrodes 8 and 9, and the working electrode 3 located within said sample flow path 7.

IV. Analytical Apparatus

The coulometric type of electrochemical detector, in which the electrode of the present invention is incorporated as shown in FIG. 8, is suitably used in combination with liquid chromatography, esp., high speed liquid chromatography (HPLC) for detecting and determining trace amounts of biosubstances.

As liquid chromatography, conventional measuring systems may be employed. For example, there is shown in FIG. 9 a double-channeled multi-stage type of detector system in which two electrochemical detectors 13 and 14 of the coulometric type, each with the electrode of the present invention built in, are connected in series to each other.

Figure 9:
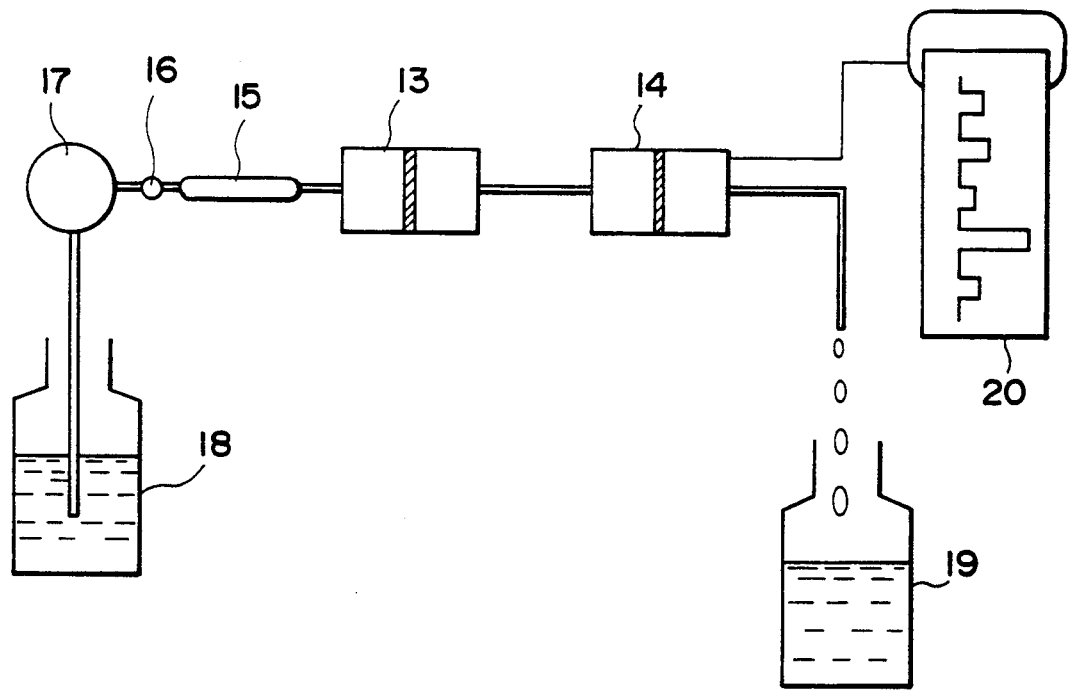
FIG. 9 is a schematic sketch illustrating an analytical apparatus according to this invention.

The system of FIG. 9 includes, in addition to the detectors 13 and 14, an analytical column 15 for liquid chromatography, a sample input port 16, a pump 17, a carrier liquid reservoir 18, a waste liquid reservoir 19 and a recorder 20.

The analytical column and carrier liquid may be arbitrarily selected depending upon the components of samples to be analyzed.

This analytical apparatus is suited for the analysis of trace components in biosubstances such as catecholamines or their metabolites. Furthermore, with a multi-stage type of detector system in which a multiplicity (2 to 30) of detectors are connected in series with one another, a plurality of components in a mixture of complicated trace components, like biosubstances, can be analyzed in a single analytical operation by applying suitable high potentials successively to the respective electrodes.

EXPERIMENTAL EXAMPLES

EXAMPLE 1

Preparation of Porous Carbon Product

Fully dried degreased cotton was pressed into a flat sheet having an average pore diameter of 38 μm and a thickness of 4 mm, which was dipped in a 20% ethanol solution of a phenol formaldehyde resin having an actual carbon ratio of 50% to incorporate the resin in the pores and then held at 80° C. for 8 hours. After that, the resulting laminate was pulled up from the dipping solution, and heated to 150° C. to set the impreganated resin.

Next, this flat sheet was heated to a temperature of 1000° C. at a heating rate of 70° C./hr, at which temperature it was held for 6 hours. Thereafter, it was again heated to a temperature of 1700° C., at which it was retained for a further 1 hour, followed by cooling to obtain a porous carbon product.

This product had a specific surface area of 0.4 m$^2$/g and an average pore diameter of 35 μm with a sharp poresize distribution wherein substantially no fine pores of 1 μm or less were present. The stack thickness Lc(002) of crystallite of 12 Å, determined by X-ray diffractometry, indicated that it has a glassy carbon structure.

Electrochemical Detector

The product obtained above was cut into a 5 mm×3 mm electrode for an electrochemical detector, which was then built in an electrochemical detector, as shown in FIG. 8, with Ag/AgCl as a reference electrode and platinum as a counter electrode. For the liquid junction of the reference and counter electrodes, a porous ceramic rod was used. Two such detectors were combined with high speed liquid chromatography to construct such a doublechanneled multi-stage type of detector system as shown in FIG. 9.

With this system, vanillylmandelic acid, homovanilic acid and 5-hydroxyindole-3-acetic acid in urine, which are the metabolites of catecholamines and serotonin, were analyzed as follows.

Figure 10:
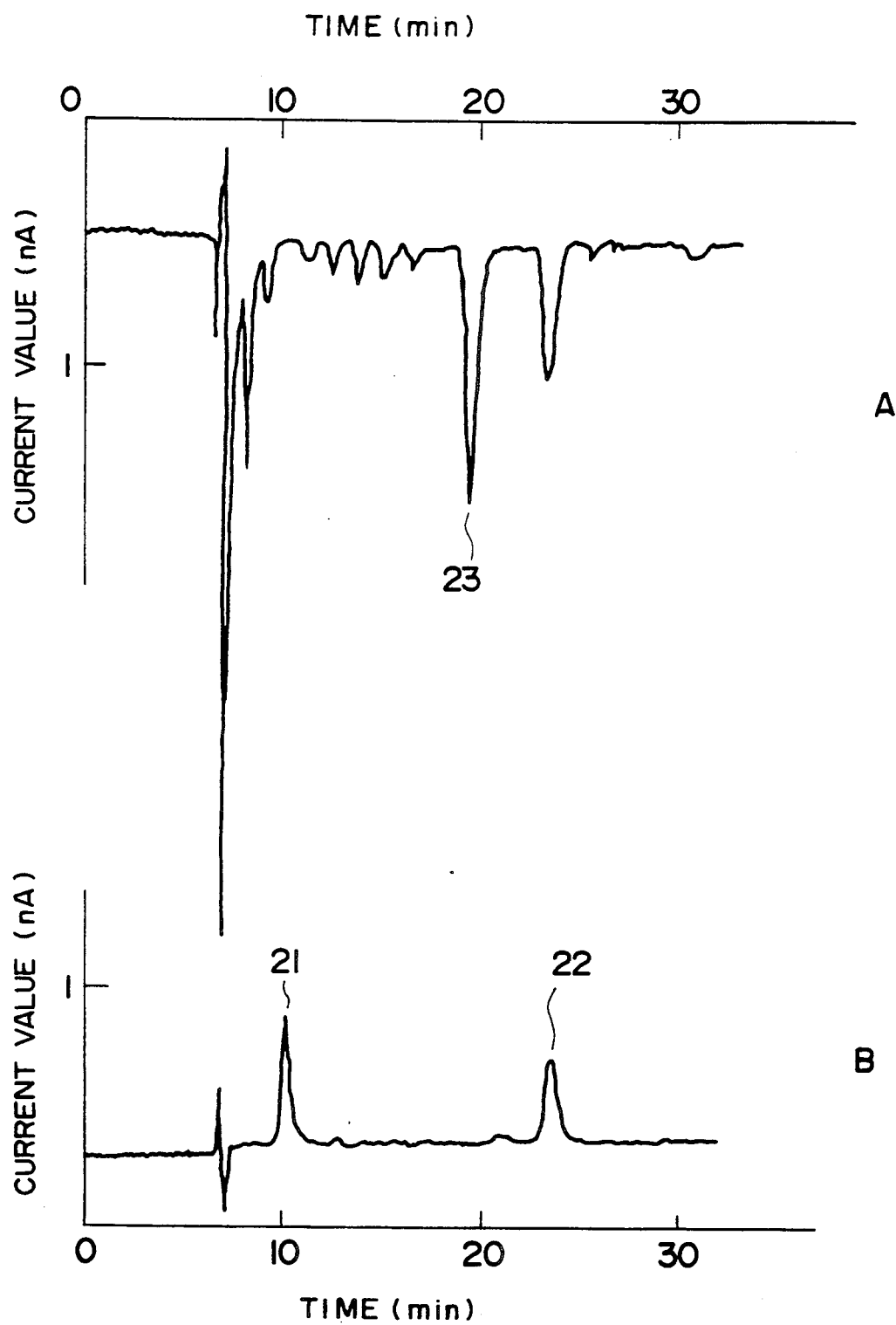
FIG. 10 is an analytical chart showing the results obtained in Example 1.
Figure 11:
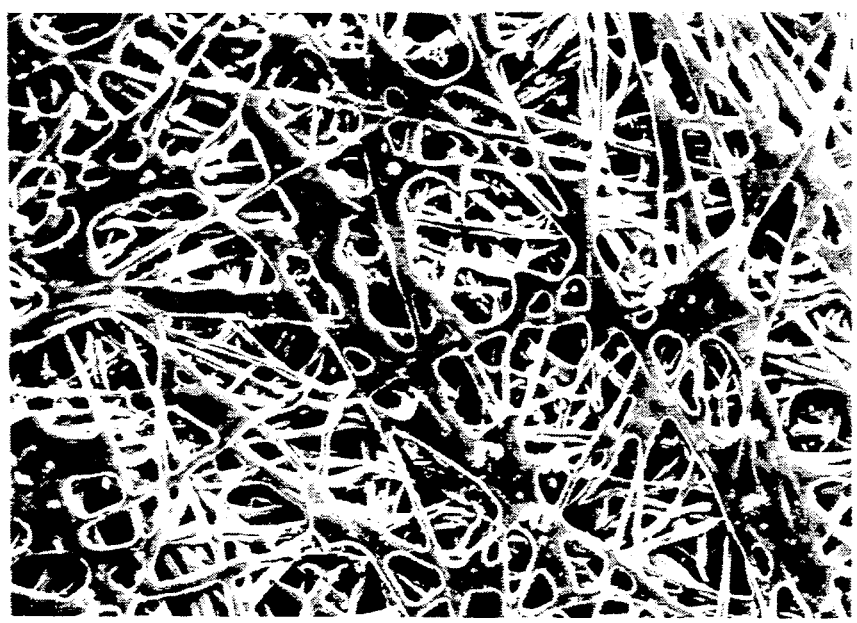
FIG. 11 is an electron micrograph showing the surface structure of the electrode obtained in Example 2.

In an isolation column filled with octadecylated silica gel through which a mixed liquid of phosphate buffer (pH: 3.1)/acetonitrile (7:1, v/v) was flowing as a carrier liquid, 0.5 μl of urine was injected, and the eluent was passed through the detectors 13 and 14 to obtain a chromatogram shown in FIG. 10. In the above operation, 670 mV and 780 mV were applied on the electrodes of the detectors 12 and 14, respectively.

As a result, since the rate of electrochemical oxidation was very high (on the order of 99% or more) with the coulometric type of detector system including the working electrodes according to the present invention, such a selective and highly sensitive chromatogram as shown in FIG. 10 could be obtained even with the direct injection of urine. In FIG. 10, A and B stand for the chromatograms of the detectors 13 and 14, respectively.

The lower limit of detection of catecholamines, serotonin and their metabolites by this system was 1 picogram or, in terms of sensitivity, this system was 500 to 1,000 times as high as conventional amperometric type of electrochemical detectors. This system could work continuously without such troubles as clogging and deterioration of electrode performance over a period as long as one month, making it possible to perform analysis with good reproducibility.

EXAMPLE 2

Preparation of Porous Carbon Product

A porous carbon product was prepared in the same manner as in Example 1 except that fully dried paper for calligraphy, instead of the degreased cotton, was pressed into a flat sheet having an average pore diameter of 50 μm and a thickness of 4 mm.

The product had a specific surface area of 1.0 m$^2$/g and an average pore diameter of 25 μm with a sharp poresize distribution, wherein substantially no fine pores of 1 μm or less were present. The stack thickness Lc(002) of crystallite of 12 Å, determined by X-ray diffractometry, indicated that it has a glassy carbon structure.

Electrochemical Detector

The product obtained above was cut into an electrode in the same manner as in Example 1, which was then built in the same detector system as used in Example 1. With this system, analysis of vanillylmandelic acid, homovanilic acid and 5-hydroxyindole-3-acetic acid was carried out according to the procedure of Example 1.

As a result, the lower limit of detection was 1 picogram. The detector system could work continuously without such troubles as clogging and deterioration of electrode performance over a period as long as one month, making it possible to perform analysis with good reproducibility.

What is claimed is:

1. An electrode for a coulometric type of electrochemical detector, comprising a porous carbon product having the following physical properties (1) to (3):
   (1) an average pore size in the range of 5 to 70 μm,
   (2) a specific surface area in the range of 0.1 to 3 m$^2$/g, as determined by the BET method, and
   (3) a stack thickness of crystallite (Lc(002)) of 40 Å or less, as determined by X-ray diffractometry.

2. An electrode as claimed in claim 1, wherein the average pore diameter is in the range of 10 to 50 μm.

3. An electrode as claimed in claim 1, wherein the specific surface area is in the range of 0.2 to 1 m$^2$/g.

4. An electrode as claimed in claim 1, wherein the stack thickness of crystallite (Lc(002)) is 20 Å or less.

5. An electrode as claimed in claim 1, wherein the porous carbon product is substantially free from any fine pores of 1 μm or less on its surface.

6. An analytical apparatus comprising a column for liquid chromatography and at least one coulometric type of electrochemical detector, said detector having an electrode comprising a porous carbon product having the following physical properties (1) to (3):
   (1) an average pore diameter in the range of 5 to 70 μm,
   (2) a specific surface area in the range of 0.1 to 3 m$^2$/g, as determined by the BET method, and
   (3) a stack thickness of crystallite (Lc(002)) of 40 Å or less, as determined by X-ray diffractometry.

7. An analytical apparatus as claimed in claim 6, wherein the average pore diameter is in the range of 10 to 50 μm.

8. An analytical apparatus as claimed in claim 6, wherein the specific surface area is in the range of 0.2 to 1 m$^2$/g.

9. An analytical apparatus as claimed in claim 6, wherein the stack thickness of crystallite (Lc(002)) is 20 Å or less.

10. An analytical apparatus as claimed in claim 6, wherein the porous carbon product is substantially free from any fine pores of 1 μm or less on its surface.

* * * * *